United States Patent [19]

Walker

[11] Patent Number: 5,438,034
[45] Date of Patent: Aug. 1, 1995

[54] QUATERNARY AMMONIUM CARBONATE COMPOSITIONS AND PREPARATION THEREOF

[75] Inventor: Leigh E. Walker, Macungie, Pa.

[73] Assignee: Lonza, Inc., Annandale, N.J.

[21] Appl. No.: 74,312

[22] Filed: Jun. 9, 1993

[51] Int. Cl.⁶ ................... A01N 33/12; C07C 211/63
[52] U.S. Cl. .......................... 504/158; 106/2; 106/15.05; 106/18.32; 252/194; 252/380; 252/403; 422/1; 424/405; 428/541; 514/642; 514/643; 564/282; 564/291
[58] Field of Search .................. 564/291, 8, 282; 514/642, 643; 504/158; 106/2, 15.05, 18.32; 252/194, 380, 403; 422/1; 424/405; 428/541

[56] References Cited

U.S. PATENT DOCUMENTS

| | | | |
|---|---|---|---|
| 2,994,699 | 8/1961 | De Benneville | 260/294.7 |
| 3,169,983 | 2/1965 | Hunter | 260/462 |
| 3,233,645 | 12/1965 | Kalberg | 252/117 |
| 3,281,458 | 10/1966 | Jordan et al. | 260/501 |
| 3,301,815 | 1/1967 | Hunyar et al. | 260/45.9 |
| 3,646,147 | 2/1972 | Dadekian | 260/583 R |
| 4,585,795 | 4/1986 | Linderborg | 514/558 |
| 4,929,454 | 5/1990 | Findlay | 424/638 |
| 5,004,760 | 4/1991 | Patton et al. | 521/149 |

FOREIGN PATENT DOCUMENTS

| | | |
|---|---|---|
| 618433 | 2/1949 | United Kingdom . |
| 650304 | 2/1951 | United Kingdom . |
| 669506 | 4/1952 | United Kingdom . |
| 719617 | 12/1954 | United Kingdom . |
| 795814 | 5/1958 | United Kingdom . |

OTHER PUBLICATIONS

L. Jin & K. Archer, "Copper Based Wood Preservatives: Observation on Fixation, Distribution and Performance" preprints for *American Wood-Preservers' Association* Apr. 1991 meeting.

(List continued on next page.)

*Primary Examiner*—Peter O'Sullivan
*Attorney, Agent, or Firm*—Darby & Darby

[57] ABSTRACT

Quaternary ammonium carbonates having the formula

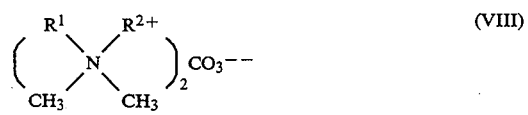

(VIII)

wherein $R^1$ is a $C_1$–$C_{20}$ alkyl or aryl-substituted alkyl group and $R^2$ is a $C_8$–$C_{20}$ alkyl group have been synthesized.

These compounds and compositions further comprising the corresponding quaternary ammonium bicarbonate

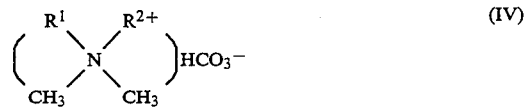

(IV)

wherein $R^1$ is the same or a different $C_1$–$C_{20}$ alkyl or aryl-substituted alkyl group and $R^2$ is the same or a different $C_8$–$C_{20}$ alkyl group and/or the corresponding quaternary ammonium metal carbonate

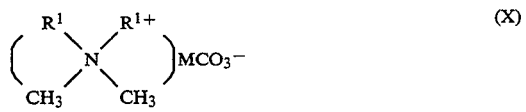

(X)

wherein $R^1$ is the same or a different $C_1$–$C_{20}$ alkyl or aryl-substituted alkyl group; $R^2$ is the same or a different $C_8$–$C_{20}$ alkyl group and M is a non-coupler metal, are prepared by reacting two reactants, a $C_1$–$C_{20}$ alkyl or aryl-substituted alkyl, $C_8$–$C_{20}$ alkyl quaternary ammonium chloride and a metal hydroxide, in a solvent comprising a $C_1$–$C_4$ normal alcohol. The amount of metal chloride reactant is that amount sufficient to yield the $C_1$–$C_{20}$ alkyl or aryl-substituted alkyl, $C_8$–$C_{20}$ alkyl quaternary ammonium hydroxide, a metal chloride, and optionally unreacted metal hydroxide. The resultant quaternary ammonium hydroxide and any unreacted metal hydroxide are then reacted with carbon dioxide to yield the quaternary ammonium carbonate and optionally metal carbonate.

Also provided is a method for preserving a wood substrate. Accordingly, the substrate is treated with a metal coupler-free wood preservative system comprising a biocidal effective amount of the carbonate quats above, preferably those prepared by the method above, and a solvent.

28 Claims, 1 Drawing Sheet

OTHER PUBLICATIONS

D. D. Nicholas et al., "Distribution and Permanency of DDAC in Southern Pine Sapwood Treated by the Full-Cell Process", *Forest Products Journal* 41 (1):41–45 (Jan. 1991).

L. Jin & A. F. Preston, "The Interaction of Wood Preservatives With Lignocellulosic Substrates" *Holzforschung* 45 (6):455–459 (1991).

*Proc. Amer. Wood–Preservers Assoc.* 80:191–209 (1984).

Y. Nakama, F. Harusawa & I. Murotani, "Cloud Point Phenomena In Mixtures of Anionic and Cationic Surfactants in Aqueous Solution" *JAOCS* 67 (11):717–721, (Nov. 1990).

A. F. Preston et al., "Recent Research On Alkylammonium Compounds In The U.S.", *American Wood–Preservers' Association*, 83:331–348 (1987).

"Quaternary Ammonium Compounds, Fine & Functional Chemicals" *AKZO*, pp. 1, 3–20 (1991).

D. D. Miller et al., "Control of Aggregate Structure With Mixed Counterions In An Ionic Double–Chained Surfactant", *Langmuir* 4(6):1363–1367 (1988).

Ewa Z. Radinska et al., "Supra–Self Assembly: Vesicle–Micelle Equilibrium", *Colloids and Surfaces* 46:213–217 (1990).

J. E. Brady et al., "Counterion Specificity As The Determinant of Surfactant Aggregation" *J. Phys. Chem.* 90:1853–1859, (1986).

D. D. Miller et al., "Fluorescence Quenching In Double–Chained Surfactants. 1. Theory of Quenching In Micelles and Vesicles" *J. Phys. Chem.* 93:323–325 (1989).

J. E. Brady et al., "Spontaneous Vesicles", *J. American Chemical Society* 106:4279–4280 (1984).

A. F. Preston, "Dialkyldimethylammonium Halides As Wood Preservatives", *JAOCS* 60 (3):567–570 (Mar. 1983).

D. D. Nicholas & A. F. Preston, "Interaction of Preservatives With Wood" *Chemistry of Solid Wood*, pp. 307–320 (1984).

E. W. Anacker and H. M. Ghose, "Counterions and Micelle Size I. Light Scattering by Solutions of Dodecyltrimethylammonium Salts", vol. 67 pp. 1713–1715, (Aug. 1963).

L. Sepulveda et al., "A New and Rapid Method for Preparing Long-Chain Alkyltrimethylammonium Salts With A Variety of Counterions", *Journal of Colloid and Interface Science* 117 (2):460–463 (Jun. 1987).

E. Jugerman et al., *Cationic Surfactants*, pp. 56–57, Marcel Dekker Inc. (1969).

"Quaternary Ammonium Compounds", *K.O.* 19:521–531 (1982).

"Quaternary Ammonium Compounds", *K.O.* 16:859–865 (1968).

Astle, "Industrial Organic Nitrogen Compounds", Reinhold Publ. pp. 64–67 (1961).

"Organic Reactions" 11, Chaptr. 5, Krieger Publ. Co., pp. 376–383 (1960).

Carl Kaiser et al., "Alkenes via Hofmann Elimination: Use of Ion–Exchange Resin For Preparation Of Quaternary Ammonium Hydroxides: Diphenylmethyl Vinyl Ether", *Organic Synthesis*, Collective vol. VI, pp. 552–554, John Wiley, Inc. (1988).

Y. Talmon et al., "Spontaneous Vesicle Formed From Hydroxide Surfactants: Evidence From Electron Microscopy" *Science* 221:1047–1048 (Sep. 9, 1983).

Awata et al., "Cathodic Esterification of Carboxylic Acids", *Chemistry Letters*, pp. 371∝374 (1985).

A. W. Ralston et al., "The Solubilities of Long–Chain Dialkyldimethyl–Ammonium Chlorides In Organic Solvents", Contribution from the Research Laboratory of Armour and Company 13:186–190 (1948).

A. W. Ralston et al., "Conductivities of Quaternary Ammonium Chlorides Containing Two Long–Chain Alkyl Groups", Contribution from the Research Laboratory of Armour and Company 70:977–979 (Mar. 1948).

*Organic Chemistry* 35:3597–3598 (1941).

T. P. Schultz et al., "Role of Stilbenes in the Natural Durability of Wood: Fungicidal Structure–Activity Relationships", *PhytoChemistry* 29:1501–1507 (1990).

85: 123253x "A Simple Preparation of Anhydrous Tetraalkylammonium Salts" (Abstract) (1976).

115: 87485b "Wood Preservatives Containing Quaternary Ammonium Salts With Polymers" (Abstract) (1991).

112: 212470j "Agrochemical Fungicides Containing Quaternary Ammonium Salts" (Abstract) (1990).

113:153776j "Microbicidal Thermoplastic Resin Compositions" (Abstract) (1990).

112: 79768u "Noncorrosive Quaternary Ammonium Compounds As Wood Preservatives" (Abstract) (1990).

113: 163999y "Capacitor Driving Electrolytes and Their Preparation" (Abstract) (1990).

112: 54969x "Preparation of Quaternary Ammonium Hydroxides Fees of Halogens" (Abstract) (1990).

110: 212114e "Process For Producing Quaternary Salts" (Abstract) (1989).

(List continued on next page.)

OTHER PUBLICATIONS

114: 246824j "Preparation of Carbonic Half-Esters of Betaine Structure" (Abstract) (1991).
98: 200032x "Didecyldimethylammonium Chloride—A Quaternary Ammonium Wood Preservative" (Abstract) (1993).
91: 152627b "Efficacy of Acidic and Alkaline Solutions of Alkylammonium Compounds As Wood Preservatives" (Abstract) (1979).
113: 154360f "Microbicidal Coating Compositions Containing Quaternary Ammonium Salts" (Abstract) (1990).
109: 124403x "Quaternary Ammonium Salt-Containing Wood Preservatives" (Abstract) (1988).
103: 109954K "Clear Aqueous Disinfectant Solutions Containing Chlorhexidine Lactate Or Gluconate And Quaternary Ammonium Salts" (Abstract) (1989).
70: 111034d "Quaternary Ammonium Bases Compatible With Scintillation-Counting Liquids" (Abstract) (1969).
60: 16447d "Nematocidal Quaternary Ammonium Salts" (Abstract) (1964).
91: 109311g "Composition For Removing Water From Surfaces Of Articles" (Abstract) (1979).
75: 119170u "Corrosion-Resistant Lubricants and Antistatic Agents" (Abstract) (1971).
66: 66227y "Stabilization of Vinyl Resins With Organic Quaternary Ammonium Nitrates" (Abstract) (1967).
66: 1953n "N-Alkyl Ammonium Humates" (Abstract) (1967).
70: 111034d "Quaternary Ammonium Bases Compatible With Scintillation-Counting Liquids" (Abstract) (1969).
97: 91725 (1982).

QUATERNARY AMMONIUM CARBONATE COMPOSITIONS AND PREPARATION THEREOF

| Table of Related Applications | | | |
|---|---|---|---|
| Appln. No. | Dated Filed | Title | Inventor |
| 08/074,313 | Concurrently herewith | Quaternary Ammonium Hydroxide Compositions and Preparation Thereof | Leigh E. Walker |
| 08/074,136 | Concurrently herewith | Quaternary Ammonium Carboxylate Compositions and Preparation Thereof | Leigh E. Walker |
| 08/074,314 | Concurrently herewith | Waterproofing and Preparation Compositions and Preparation Thereof | Leigh E. Walker |

1. Field of the Invention

This invention relates to the indirect synthesis of $C_1$–$C_{20}$ alkyl or aryl-substituted alkyl, $C_8$–$C_{20}$ alkyl quaternary ammonium carbonate compositions from corresponding quaternary ammonium chlorides. Di $C_8$–$C_{12}$ alkyl quaternary carbonate compositions, including those prepared by the method of the present invention, are particularly useful in wood preservative systems, as surfactants and as biocides.

2. Background of the Invention

Quaternary ammonium compounds (quats), and particularly didecyldimethylammonium chloride (DDAC)

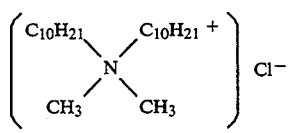

could be used as wood preservatives, if they were stable, because they possess resistance properties to fungi and termites, to loss of strength, and to electrical sensitivity similar to those of commonly used acidic copper/chromium/arsenic solution (CCA) or ammoniacal copper and arsenic salt solution preservatives. See Proc of the Am. Wood Pres. Assoc., 80:191–210 (1984). Although chloride quats do not include potentially dangerous heavy metals, didecyldimethylammonium chloride leaches rapidly in soil (Nicholas et al., Forest Prod. J., 41:41 (1991), and therefore, does require coupling with copper salt.

Findlay et al., U.S. Pat. No. 4,929,454, disclose a method of preserving wood by impregnation with a quaternary ammonium compound and at least one of zinc and copper, wherein the quat anion is chosen from the group consisting of hydroxide, chloride, bromide, nitrate, bisulfate, acetate, bicarbonate, and carbonate, formate, borate and fatty acids. These quats have distinct environmental and safety advantages over commonly used acidic copper/chromium/arsenic solution (CCA) or ammoniacal copper and arsenic salt solution preservatives in that potentially dangerous heavy metals are not included. The Findlay et al. quats require copper or zinc in order to render them relatively insoluble and to prevent them from leaching out of a treated substrate. The use of copper or zinc in the above formulations may yet raise environmental and corrosion concerns.

Additionally, didecyldimethylammonium chloride tends to absorb preferentially to the surface of the wood and does not uniformly treat the whole substrate. Finally, DDAC treated wood shows surface erosion or ages upon exposure to light. See Preston et al., Proc. Am. Wood Pres. Assoc., 83:331 (1987).

The biocidal activities of various chloride quats against bacteria, fungi, and algae are tabulated in Cationic Surfactants, E. Jungerman Ed., pp. 56–57, Marcel Dekker, Inc., 1969. Nicholas, "Interaction of Preservatives with Wood," Chemistry of Solid Wood, Advance in Chemistry Series #207, Powell ed., (A.C.S. 1984) notes that didecyldimethyl ammonium compounds and particularly DDAC are potential biocides. Preston, J.A.O.C.S. 60:567 (1983) concurs and suggests that maximum fungitoxicity is exhibited with dialkyldimethyl compounds having $C_{10}$–$C_{12}$ alkyl groups. Butcher et al., Chem Abstracts No. 91:152627b, suggests that the presence of an acid or a base can affect the activity of didecyldimethyl-ammonium quats.

Quaternary ammonium compounds (quats) are typically prepared by the reaction:

$$R^1R^2R^3N + R^4X \rightarrow R^1R^2R^3R^4NX \qquad (II)$$

wherein X is a halogen, a sulfate, a sulfo compound, or the like. When at least one of $R^1$, $R^2$, $R^3$, or $R^4$ is $C_{12}$ or longer, the product is an inert soap. Many of the inert soaps have biocidal activity against bacteria, fungi, algae, and related organisms.

Reaction (II) above is limited by the reactant $R^4X$ because $R^4$ must react with tertiary amines. For example, methyl chloride ($R^4X=CH_3Cl$) will react with a tertiary amine at less than 100° C. to yield a quaternary compound $R_3N^+CH_3Cl^-$, while methanol or methyl acetate ($R^4X=CH_3OH$ or $CH_3COOCH_3$) will not, under similar reaction conditions.

General quaternary ammonium compounds with a sulfo group are easily prepared either by the reaction of a sulfate compound with a tertiary amine (III) or by a double exchange (IV).

$$R_3N + RSO_3CH_3 \rightarrow R_3NCH_3^+ RSO_3^- \qquad (III)$$

$$R_3N^+CH_3Cl^- + RSO_3^-Na^+ \rightarrow R_3NCH_3^{+\cdot} RSO_3^- + NaCl \qquad (IV)$$

If trimethylamine is heated with carbon dioxide and methanol above 200° C. and at 85 to 95 atmospheres, the carbonate quat, bis-tetramethylammonium carbonate, is prepared. Industrial Organic Nitrogen Compounds, Astle Ed. p 66, Reinhold Inc, 1961. However, this reaction is limited to the methyl compound because higher homologs decompose to olefins by the Hofman elimination reaction. See, Organic Reactions, 11, Chptr. 5, 377, Krieger Publishing Co., 1975.

Chem Abst. 110, 212114 (1989) suggests that dimethyl carbonate will react with triethylamine in methanol in twelve hours at 115° C. and under pressure to yield a methyl carbonate quat ester.

Chem Abst. 114, 24824 (1991) discloses that 6-hydroxyhexyldimethylamine reacts with dimethyl carbonate to yield a carbonate ester quat.

Quaternary ammonium hydroxides (hydroxy quats), the intermediate in the reaction scheme of the present invention, are currently prepared by the reaction of quaternary ammonium iodide with silver oxide (V).

$$RN^+(CH_3)_3I^- + AgO \rightarrow RN^+(CH_3)_3OH^- + AgI \qquad (V)$$

However, this reaction is costly, and it is difficult to recover the silver reagent. See, *Organic Reactions,* 11:Chptr 5, pp. 376–377, Krieger Publishing Co., 1975.

In an olefin synthesis, it has been suggested to treat a quaternary salt with aqueous sodium or potassium hydroxide followed by pyrolysis in order to form the hydroxy quat and then to decompose the hydroxy quat directly. However, in this method the hydroxy quat is not isolated and the conditions for its preparation are undesirable. See, *Organic Reactions,* 11:Chptr 5, pp. 376–377, Krieger Publishing Co., 1975.

Talmon et al., *Science,* 221, 1047 (1983), have used an ion exchange resin to convert didecyldimethylammonium bromide to didecyldimethylammonium hydroxide (VI).

(VI)

However, 50 ml of ion exchange resin and two treatment steps were required to convert 3 grams of quaternary ammonium chloride to the corresponding hydroxide. See also, *Organic Synthesis,* Collective Volume VI, 552, John Wiley Inc., 1988; Brady et al. *J. Am. Chem. Soc.,* 106:4280–4282, 1984; Brady et al. *J. Phys. Chem.,* 90:9, 1853–1859, 1986; Miller et al. *J. Phys. Chem,* 91:1, 323–325, 1989; Radlinske et al. *Colloids and Surfaces,* 46:213–230, 1990.

Alternatively, quaternary ammonium hydroxide compositions have been prepared by treating a haloquat in an electrochemical cell with special cation exchange diaphragms between the cells. The hydroxy quat collects at one electrode, and the halide collects at the other. See, Japanese Patent Publication No. 02-106,915; Awata et al., *Chemistry, Letters,* 371 (1985).

Japanese Patent Publication No. 01-172,363 discloses the preparation of relatively low yields of tetraethylammonium hydroxide by reacting triethylamine with diethyl sulfate, heating the resultant quat with sulfuric acid to yield the sulfate quat, and reacting the sulfate quat with barium hydroxide to yield the short chain quat, tetraethylammonium hydroxide, and barium sulfate.

Di $C_8$–$C_{12}$ alkyl quaternary ammonium hydroxides prepared by ion exchange were used as strong bases to digest animal tissue by Bush et al., French Patent Publication No. 1,518,427.

Akzo discloses that the addition of a metallic hydroxide to a quaternary ammonium chloride such as didecyldimethylammonium chloride, in an aqueous medium, results in an equilibrium mixture of quaternary ammonium chloride and quaternary ammonium hydroxide (VII). This reaction can be driven to the right by the use of isopropanol as a solvent.

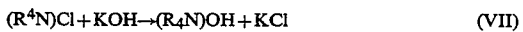

(VII)

It has now been discovered that useful $C_1$–$C_{20}$ alkyl or aryl-substituted alkyl, $C_8$–$C_{20}$ alkyl quaternary ammonium carbonates can be prepared, particularly by indirect synthesis from $C_1$–$C_{20}$ alkyl or aryl-substituted alkyl, $C_8$–$C_{20}$ alkyl quaternary ammonium chlorides, through $C_1$–$C_{20}$ alkyl or aryl-substituted alkyl, $C_8$–$C_{20}$ alkyl quaternary ammonium hydroxide intermediates. It has further been discovered that di $C_8$–$C_{12}$ alkyl quaternary ammonium carbonate quats are useful in wood preservative systems as they have improved leaching resistance, particularly without the use of the commonly used metal stabilizers or couplers, arsenic, chromium, copper, and zinc or combinations thereof.

SUMMARY OF THE INVENTION

Quaternary ammonium carbonates having the formula

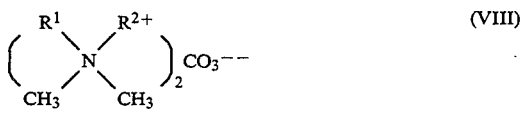

(VIII)

Figure 1A:
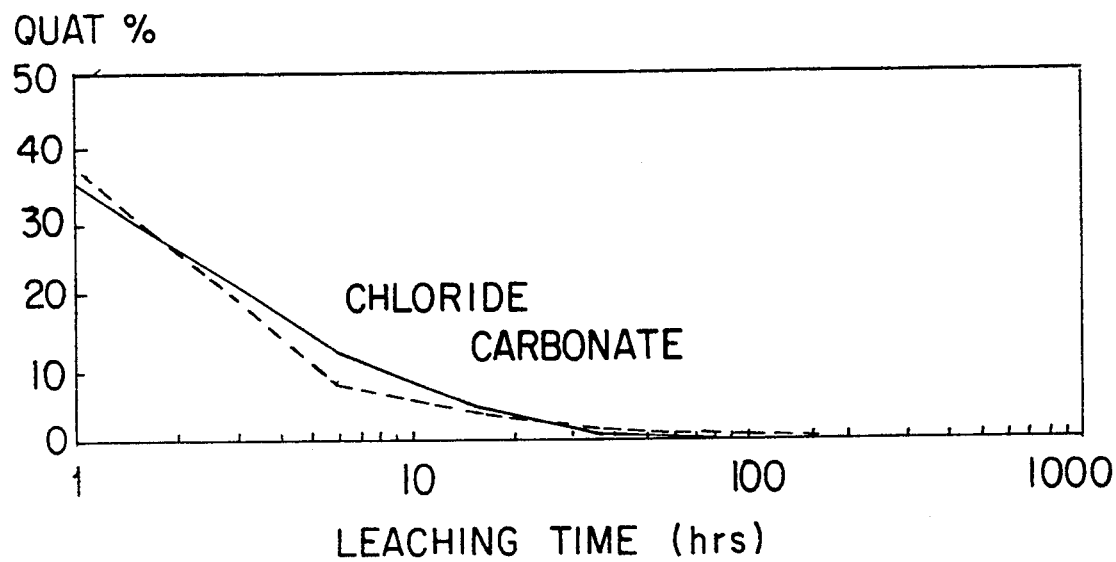
FIG. 1A is a graphic comparison of leaching of a wood preservative system according to the present invention and a wood preservative system of the prior art.

wherein $R^1$ is a $C_1$–$C_{20}$ alkyl or aryl-substituted alkyl group and $R^2$ is a $C_8$–$C_{20}$ alkyl group, and preferably wherein $R^1$ is the same as $R^2$ and $R^1$ is a $C_8$–$C_{12}$ alkyl group, as well as compositions further comprising the corresponding quaternary ammonium bicarbonate

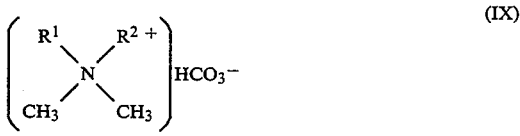

(IX)

wherein $R^1$ is the same or a different $C_1$–$C_{20}$ alkyl or aryl-substituted alkyl group as above and $R^2$ is the same or a different $C_8$–$C_{20}$ alkyl group as above, but preferably wherein $R_1$ is the same as $R^2$ and $R^1$ is a $C_8$–$C_{12}$ alkyl group; and/or the corresponding quaternary ammonium metal carbonate

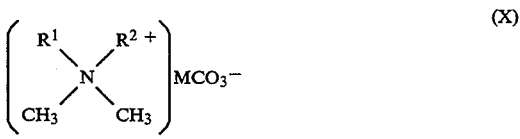

(X)

wherein $R^1$ is the same or a different $C_1$–$C_{20}$ alkyl or aryl-substituted alkyl group and $R^2$ is a $C_8$–$C_{20}$ alkyl group; but preferably wherein $R^1$ is the same as $R^2$ and $R^1$ is a $C_8$–$C_{12}$ alkyl group and M is a mono-, bi-, or trivalent metal, preferably a monovalent metal, and most preferably an alkali metal, are prepared by reacting two reactants, (a) $C_1$–$C_{20}$ alkyl or aryl-substituted alkyl, $C_8$–$C_{20}$ alkyl quaternary ammonium chloride and preferably a di $C_8$–$C_{12}$ alkyl quaternary ammonium chloride and (b) a metal hydroxide, in a solvent comprising a $C_1$–$C_4$ normal alcohol. The amount of metal hydroxide reactant is that amount sufficient to yield the corresponding $C_1$–$C_{20}$ alkyl or aryl-substituted, $C_8$–$C_{20}$ alkyl quaternary ammonium hydroxide, and preferably the corresponding di $C_8$–$C_{12}$ alkyl quaternary ammonium hydroxide, a metal chloride, and optionally unreacted metal hydroxide. The resultant quaternary ammonium hydroxide and any unreacted metal hydroxide are then reacted with carbon dioxide to yield the corresponding quaternary ammonium carbonate, optionally the corresponding quaternary ammonium bicarbonate, and optionally the corresponding quaternary ammonium metal carbonate, or a combination of any of the foregoing, and optionally metal carbonate.

Also contemplated by the invention is a method for preserving a wood substrate. Accordingly, the substrate is treated with a metal coupler-free wood preservative system which comprises (a) a biocidal effective amount of at least one of the above di $C_8$–$C_{12}$ alkyl quaternary ammonium carbonate compounds or compositions, and preferably those prepared by the method above, and (b) a solvent.

DETAILED DESCRIPTION OF THE INVENTION

Quaternary ammonium carbonate (carbonate quats) having the formula

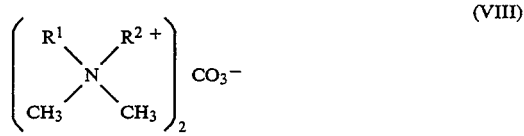

(VIII)

wherein $R^1$ and $R^2$ are the same $C_8$–$C_{12}$ alkyl group, have been identified for use as wood preservatives. These carbonate quats do not require metal couplers to render them leach resistant.

A preferred carbonate quat is didecyldimethylammonium carbonate wherein $R^1$ and $R^2$ are a $C_{10}$ alkyl group and most preferably an n—$C_{10}$ alkyl group. Didecyldimethylammonium carbonate, when observed as a 70–80 percent by weight solution in a 5–7 percent by weight alcohol/15–20 percent by weight water is a yellow/orange liquid that has a slightly fruity odor. This formulation has a flash point of about 160° F., and it reacts with carboxyl containing compounds.

The stability, and particularly the thermal stability, of carbonate quats is far superior to that of hydroxy quats, making these carbonate quats suitable for concentrating and as stock intermediates for further processing.

One or more of these carbonate quats alone or in combination with the corresponding bicarbonate quat(s) and/or metal carbonate salt(s), preferably potassium carbonate salt, can be formulated as metal coupler-free wood preservative systems. These systems include biocidal effective amounts of at least one carbonate quat and a suitable solvent, including aqueous and non-aqueous solvents. Preferably, the solvent is an aqueous solvent including, but not limited to, water, aqueous alcohol such as aqueous ethanol, ammonia water, and the like, or a combination of any of the foregoing.

Although other conventional additives may be added as required for application to different substrates and for different uses as known to those of ordinary skill in the art, metal stabilizers are not required and, in fact, are not recommended to inhibit leaching of the quat from the substrate. Accordingly, wood substrates, such as lumber, timber, and the like, can be treated with metal coupler-free preservative systems which comprise the above carbonate quat(s) diluted in a suitable solvent as above.

The amount of di $C_8$–$C_{12}$ alkyl quaternary ammonium carbonate(s) used to treat the substrate is a biocidal effective amount, i.e. that amount effective to inhibit the growth of or to kill one or more organism that causes wood rot, to inhibit sap stain, or a combination thereof. Such organisms include, but are not limited to, *Trametes viride* or *Trametes versicolor*, which cause a white rot; *Goeophyllium trabeum*, which causes a brown rot; and *Aspergillus niger*, which causes sap stain/mold.

Typically, a wood preservative system will comprise from about 0.1 to about 5 parts by weight of the carbonate quat(s) and from about 95 to about 99.9 parts by weight of solvent based upon 100 parts by weight of quat and solvent combined. Most preferably, the wood preservative system of the present invention will comprise from about 1 to about 2 parts by weight of carbonate quat(s) and from about 98 to about 99 parts by weight of solvent on the same basis.

Treatment of the substrate is accomplished by any means known to those of ordinary skill in the art including, but not limited to, dipping, soaking, brushing, pressure treating, or the like. The length of treatment required will vary according to treatment conditions, the selection of which are known to those skilled in the art.

The metal coupler-free preservative systems of the present invention display greater resistance to leaching than wood preservatives currently used in the industry. Resistance to leaching is defined as retention of a biocidal effective amount, and preferably at least about 2% by weight, of carbonate quat(s) in the substrate over a prolonged period of at least about 100 hours and preferably about 350 hours. Applicants hypothesize, without being bound by any theory, that the carbonate quat reacts or complexes with the woody matrix of the substrate, thereby "fixing" it in the substrate. It is also believed that the long chain carbonate quat(s) and the wood preservative systems that include such quats enhance water-proofing properties of treated substrates.

Although certain carbonate quats can be prepared by a variety of methods, applicants have discovered an indirect synthesis method that can be used to prepare a variety of $C_1$–$C_{20}$ alkyl or aryl-substituted alkyl, $C_8$–$C_{20}$ alkyl quaternary ammonium carbonate compounds, preferably di $C_8$–$C_{12}$ alkyl quaternary ammonium carbonate compounds, and most preferably didecyldimethylammonium carbonate.

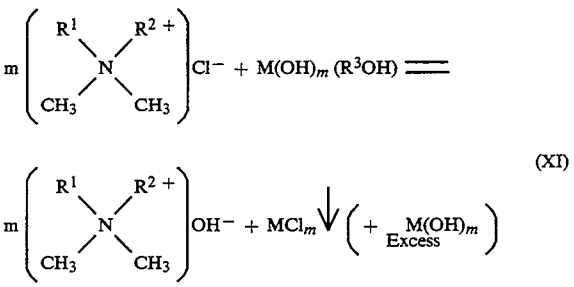

(XI)

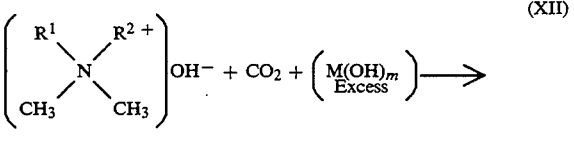

(XII)

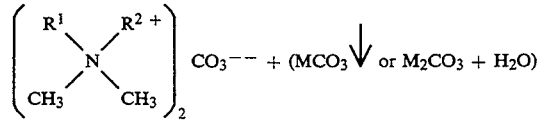

wherein $R^1$ is a $C_1$–$C_{20}$ alkyl or aryl-substituted alkyl group; is a $C_8$–$C_{20}$ alkyl group; and preferably $R^1$ is the same as $R^2$ and $R^1$ is a $C_8$–$C_{12}$ alkyl group; $R^3$ is a straight chain $C_1$–$C_4$ alkyl group; M is a mono-, bi-, tri-valent metal, preferably a monovalent metal, and most preferably an alkali metal; and m is 1 if M is monovalent, 2 if M is di-valent, and 3 if M is trivalent.

A $C_1$–$C_{20}$ alkyl or aryl-substituted alkyl, $C_8$–$C_{20}$ alkyl, and preferably a di $C_8$–$C_{12}$ alkyl, quaternary ammonium chloride is used as a starting material and is reacted with a metal hydroxide to yield a $C_1$–$C_{20}$ alkyl or aryl-substituted alkyl, $C_8$–$C_{20}$ alkyl, and preferably a di $C_8$–$C_{12}$ alkyl, quaternary ammonium hydroxide intermediate. The hydroxy quat intermediate(s) and any excess metal hydroxide are then reacted with carbon dioxide to yield the carbonate quat(s) and the metal carbonate.

Many di $C_8$–$C_{12}$ alkyl quaternary ammonium chlorides are suitable reactants to prepare the intermediate hydroxy quat, but didecyldimethylammonium chloride is preferred. The selections of the $R^1$ and $R^2$ substituents of the chloride quat reactant are determinative of the hydroxy quat intermediate, and therefore, of the carbonate quat product.

Special mention is also made of processes wherein $R^1$ is a methyl, $C_8$ alkyl, $C_9$ isoalkyl, $C_{10}$ alkyl, $C_{12}$ alkyl, $C_{14}$ alkyl, $C_{16}$ alkyl, or benzyl group; and $R^2$ is a $C_{10}$ alkyl, $C_{12}$ alkyl, $C_{14}$ alkyl, or $C_{16}$ alkyl group.

The metal hydroxide reactant is a mono-, bi-, or trivalent metal hydroxide, preferably a mono-valent metal hydroxide, and most preferably an alkali metal hydroxide such as sodium hydroxide or potassium hydroxide. Special mention made of potassium hydroxide. The metal chloride first step reaction product will precipitate and is easily removed, i.e. by filtration or the like, yielding a hydroxy quat/solvent reaction product. The hydroxy quat can be separated therefrom by drying or the like, if desired.

The first reaction (XI) is conducted in a solvent which comprises a $C_1$–$C_4$ normal alcohol. Preferably the solvent is ethanol, and most preferably, anhydrous ethanol. The reaction to form the hydroxy quat is typically an equilibrium reaction, but the use of a $C_1$–$C_4$ normal alcohol solvent drives the reaction sharply to the hydroxy quat.

The amount of metal hydroxide reactant typically is a stoichiometric amount with respect to the di $C_8$–$C_{12}$ alkyl quaternary ammonium chloride reactant. Therefore, on a theoretical basis and if the reaction were complete and unequilibrated, there would be no excess of metal hydroxide reactant upon completion of the intermediate reaction. In practice, yield when using a stoichiometric amount of metal hydroxide reactant will range from about 65% to about 95%, but will vary, dependent, in part, upon the particular metal hydroxide reactant.

Yield of the hydroxy quat can be further improved over conventional methods by utilization of a stoichiometric excess of metal hydroxide ranging from about 2% to about 20% excess. If an excess of metal hydroxide is used yield will be increased to from about 95% to about 99%, again varying as above.

The unreacted metal hydroxide is soluble in the hydroxy quat/solvent intermediate.

Hydroxy quat and any unreacted metal hydroxide are then reacted with at least a stoichiometric equivalent of carbon dioxide to yield the quaternary ammonium carbonate(s), and if any unreacted metal hydroxide were present, the metal carbonate(s), The conversion of the metal hydroxide to the metal carbonate is the preferred reaction of the two carbonations and will proceed more rapidly. The metal carbonate will precipitate and can be separated easily, i.e. by filtration or the like, leaving the stable carbonate quat(s) or carbonate quat(s)/solvent reaction product.

The carbonation step can also produce the bicarbonate quat or the metal carbonate quat as byproducts. The carbonate quat alone or in combination with the bicarbonate quat and/or the metal carbonate quat are suitable for use in the metal coupler-free wood preservative systems of the present invention. These carbonate quats or carbonate/bicarbonate/metal carbonate compositions, do not require a metal coupler for stabilization in a wood substrate. Completely metal-free wood preservative systems are preferred. However, if a metal carbonate quat is included in the system, preferably the metal is not a metal currently used as a coupler, and most preferably, it is an alkali metal and does not pose environmental or corrosion hazards or concerns.

Mixing, adding, and reacting of the components in the present invention can be accomplished by conventional means known to those of ordinary skill in the art. The order of addition of reactants or solvent in any individual step does not affect the process. Reactants and/or solvent can be added sequentially or simultaneously in any suitable reaction vessel. For example, the metal hydroxide may be dissolved in alcohol and the resultant mixture added to the chloride quat or the chloride quat may be dissolved in alcohol and the metal hydroxide added to the resultant mixture. Importantly, the method of the present invention is suitable for commercial scale production techniques and equipment, yet convenient for small scale work.

Typically, the reactants and solvent of the chloride quat to hydroxy quat reaction (XI) will be stirred and heated to from about 20° C. to about 70° C. and held at that temperature for a period of from about 1 hour to about 5 hours. The reaction mixture is then cooled, first to room temperature and then to about 0° C. where it is held for about 1 hour to about 2 hours. Any precipitated metal chloride is collected as is known in the art, i.e. such as by filtration.

Alternatively, the first reaction reactants and solvent can be stirred at a slightly elevated temperature, i.e. from about 20° C. to about 40° C., to yield the hydroxy quat/solvent mixture. Hydroxy quat can be separated as above.

The carbon dioxide is generally bubbled for a suitable period known to those of ordinary skill in the art through the hydroxy quat/solvent supernatant after the metal chloride precipitate has been separated. Alternatively, the carbon dioxide can be added as solid dry ice directly to the hydroxy quat. Typically, this time varies from about 0.5 hour to about 1 hour at ambient temperature. Any precipitated metal carbonate is collected as is known in the art, i.e. such as by filtration.

DESCRIPTION OF THE PREFERRED EMBODIMENTS

The following examples illustrate the invention without limitation. All parts and percentages are given by weight unless otherwise indicated.

Quaternary compounds are quantified by two phase titration with sodium laurylsulfate and an indicator. The mixture is buffered to a pH of 10.

PREPARATION OF CARBONATE QUATS

EXAMPLE 1

180 grams (0.4 moles) of 80% didecyldimethylammonium chloride in 20% ethanol water (144 grams DDAC), 180 ml of absolute denatured ethanol (denatured with methanol/isopropanol), and 32 grams (0.49 mole) of 85% potassium hydroxide pellets (27 grams KOH) were mixed in a flask that was purged with nitrogen and equipped with a heating mantle and a magnetic stirrer. The mixture was stirred and heated at 60°–70° C. for three hours. The mixture was then allowed to cool to room temperature and finally cooled to 5° C.

Potassium chloride precipitated, and the precipitate was collected on a vacuum filter. The solid was washed with cold ethanol and subsequently was dried, yielding 31 grams (calculated yield 29.6 grams) of dry potassium chloride.

The ethanolic solution of the hydroxy quat containing about 0.09 mole of unreacted KOH, was stirred while 50 grams of carbon dioxide (from sublimed carbon dioxide) were bubbled over one half hour. The resultant mixture was then filtered to remove 7.2 grams of potassium carbonate (6.2 grams calculated), and the filtrate was concentrated to yield an orange/brown liquid with 80–85% carbonate quat in water/ethanol and less than 0.1% chloride quat having a product with 98 to 99% exchanged quat purity.

EXAMPLE 2

180 grams (0.4 moles) of 80% didecyldimethylammonium chloride in 20% ethanol water (144 grams DDAC), 180 ml of absolute denatured ethanol (denatured with methanol/isopropanol), and 32 grams (0.49 mole) of 85% potassium hydroxide pellets (27 grams KOH) were mixed in a flask that was purged with nitrogen and equipped with a heating mantle and a magnetic stirrer. The mixture was heated to 50° C. and stirred for one hour.

Potassium chloride precipitated, and the precipitate was collected on a vacuum filter. The solid was washed with cold ethanol and subsequently was dried, yielding 31 grams (calculated yield 29.6 grams) of dry potassium chloride.

The ethanolic solution of the hydroxy quat containing about 0.09 mole of unreacted KOH, was stirred while 50 grams of carbon dioxide (from sublimed carbon dioxide) were bubbled over one half hour. The resultant mixture was then filtered, and the filtrate was concentrated to yield an orange/brown liquid. Yield was similar to that of Example 1.

EXAMPLE 3

The procedure of Example 1 is followed substituting 0.4 moles of 80% octyldecyldimethylammonium chloride for the didecyldimethylammonium chloride to yield octyldecyldimethylammonium carbonate.

EXAMPLE 4

The procedure of Example 1 is followed substituting 0.4 moles of 80% isononyldecyldimethylammonium chloride for the didecyldimethylammonium chloride to yield isononyldecyldimethylammonium carbonate.

EXAMPLE 5

The procedure of Example 1 is followed substituting 0.4 moles of 80% benzyldodecyldimethylammonium chloride for the didecyldimethylammonium chloride to yield benzyldodecyldimethylammonium carbonate.

EXAMPLE 6

The procedure of Example 1 is followed substituting 0.4 moles of 80% of a mixture of benzyldodecyl-; benzyltetradecyl-; and benzylhexadecyldimethylammonium chloride for the didecyldimethylammonium chloride to yield a mixture of benzyldodecyl-; benzyltetrabutyldecyl-; and benzylhexadecyldimethylammonium carbonate.

EXAMPLE 7

The procedure of Example 1 is followed substituting 0.4 moles of 80% dihexadecyldimethylammonium chloride for the didecyldimethylammonium chloride to yield dihexadecyldimethylammonium carbonate.

EXAMPLE 8

The procedure of Example 1 is followed substituting 0.4 moles of 80% dodecyltrimethylammonium chloride for the didecyldimethylammonium chloride to yield dodecyltrimethylammonium carbonate.

TREATMENT OF WOOD SUBSTRATES

EXAMPLE 9

End grain pine wafers were weighed and then soaked with didecyldimethylammonium carbonate until a weight gain of was observed.

The treated wafers were then placed in water and weighed periodically to determine resistance to leaching.

Figure 1B:
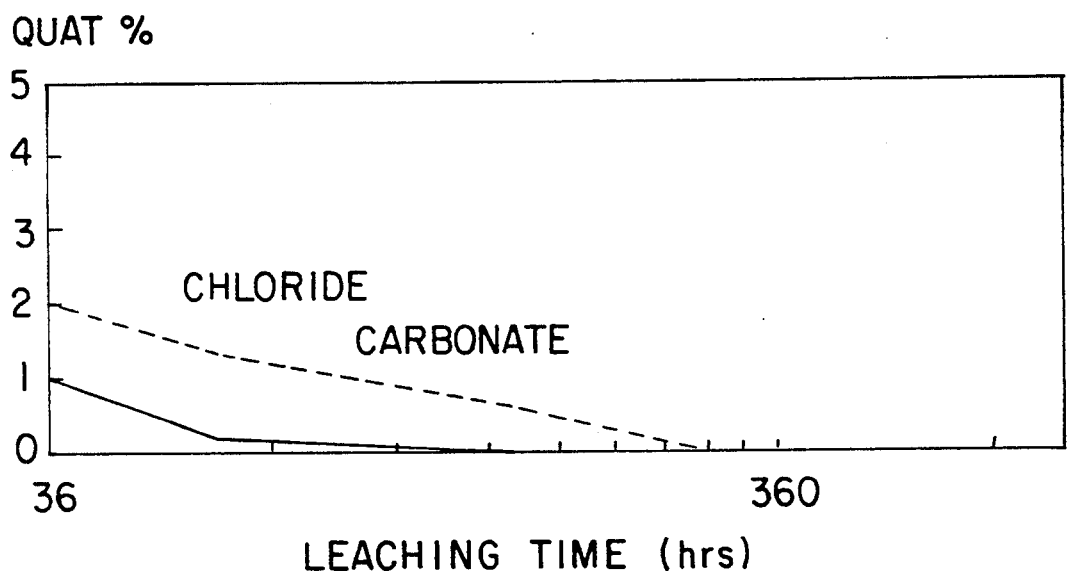
FIG. 1B is an enlarged segment of the graph of FIG. 1A.

Results are illustrated in FIGS. 1A and 1B.

COMPARATIVE EXAMPLE 9A

The procedure of Example 9 was followed substituting didecyldimethylammonium chloride for the didecyldimethylammonium carbonate.

Results are illustrated in FIGS. 1A and 1B.

FIGS. 1A and 1B illustrate that the carbonate quat resists leaching for extended periods while the chloride quat leaches to levels of 1% or less in a relatively short period.

EXAMPLES 10 AND 11 AND COMPARATIVE EXAMPLES 10A, 10B, 11A AND 11B

A 10"×0.5"×0.75" piece of ponderosa pine was equilibrated, weighed, and heated for two hours at 60° C. The wood was treated with a treating solution of 2% didecyldimethylammonium carbonate in water solvent by heating in the solution at 60° C. to 80° C. for one hour, cooling and standing overnight, and then being subjected to a second warm to cool cycle. The samples were allowed to dry to constant weight, and the uptake was determined by comparing starting and finishing weights.

The samples were then heated for two hours at 60° C., and the weight of the warm treated samples was compared to the oven dried sticks before treatment.

Additional examples were prepared either omitting the carbonate quat, substituting a chloride quat, or using 1% quat in a 3% aqueous ammonia solvent.

Formulations and results are illustrated in Table 1.

TABLE 1

| | Weight Uptake from Quat Solutions | | | | | |
|---|---|---|---|---|---|---|
| Example | 10 | 10A | 10B | 11 | 11A | 11B |
| Solvent | Water | Water | Water | 3% Ammonia | 3% Ammonia | 3% Ammonia |
| Quat | Carbonate | — | Chloride | Carbonate | — | Chloride |
| Weight Uptake (%) | 1.8 | −0.4 | 0.6 | 1.6 | −0.6 | 2.0 |

Examples 10 and 11, when compared with Comparative Examples 10A, 10B, 11A, and 11B respectively, illustrate the ability of the carbonate quats of the present invention to be applied to wood substrates. The carbonate quat is absorbed better than the chloride quat in water, and is absorbed similarly to the art accepted chloride quat in ammonia/water. However, the carbonate quats can be used without metal coupling agents in treating wood substrates.

EXAMPLES 12–15 AND COMPARATIVE EXAMPLES 12A, 12B, 15A and 15B

A piece of wood was treated according to the procedure of Example 10. The piece of wood was then soaked in water at room temperature for 24 hours, dried to constant weight, and weighed to determine how much chemical remained. The piece of wood was soaked for 96 additional hours (120 hours total), dried to constant weight, and weighed to determine the leaching of quat from the treated wood. The water was changed several times during this period.

Additional examples were prepared with different quat concentrations, different anions, and different solvents.

Formulations and results are illustrated in Table 2.

TABLE 2

| | Leaching of Quat | | | | | | | |
|---|---|---|---|---|---|---|---|---|
| Example | 12 | 12A | 12B | 13 | 14 | 15 | 15A | 15B |
| Solvent | Water | Water | Water | Water | Water | 3% Ammonia | 3% Ammonia | 3% Ammonia |
| Quat | 2% Carbonate | | 2% Chloride | 2.5% Carbonate | 5% Carbonate | 2% Carbonate | | 2% Chloride |
| Weight Uptake (%) | 1.8 | 0.4 | 0.6 | 1.1 | 1.8 | 1.6 | 0.6 | 2 |
| Retained Quat at 24 Hours (Absolute %/ Relative %) | 2/110 | −0.2/— | 0.5/83 | —/100+ | —/100 | 1.7/100 | −0.3/— | 1.7/85 |
| Retained Quat at 120 Hours (Absolute %/ Relative %) | 1.6/80 | −0.2/— | 0.4/67 | —/— | —/— | 1.2/75 | −0.3/— | 1.36/65 |

Examples 12–15 and particularly Example 12, when compared with Comparative Examples 12A and 12B, and Example 15, when compared with Comparative Examples 15A and 15B, demonstrate the improved retention properties of carbonate quats over conventional chloride quats, particularly in the absence of metal stabilizers.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

I claim:

1. A wood preservative composition comprising
   (a) at least one di $C_8$–$C_{12}$ alkyl quaternary ammonium carbonate having the formula

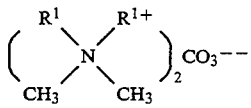

wherein $R^1$ is a $C_8$–$C_{12}$ alkyl group; and
   (b)(1) at least one di $C_8$–$C_{12}$ alkyl quaternary ammonium bicarbonate having the formula

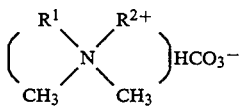

wherein $R^1$ is the same or a different $C_8$–$C_{12}$ alkyl group as in (a); or
   (2) at least one di $C_8$–$C_{12}$ alkyl quaternary ammonium metal carbonate having the formula

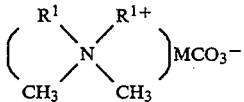

wherein $R^1$ is the same or a different $C_8$–$C_{12}$ alkyl group as in (a) or (b) and M is a non-coupler metal, or
   (3) a combination of (b)(1) and (b)(2);
said composition being metal coupler-free.

2. A wood preservative composition as defined in claim 1 wherein (a) is didecyldimethylammonium carbonate, (b)(1) is didecyldimethylammonium bicarbonate, and (b)(2) is didecyldimethylammonium potassium carbonate salt.

3. A wood preservative system comprising a (A) biocidal effective amount of at least one di $C_8$–$C_{12}$ alkyl quaternary ammonium carbonate having the formulation

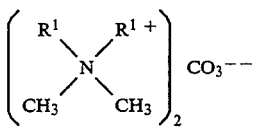

wherein $R^1$ is a $C_8$–$C_{12}$ alkyl group and (B) a solvent; wherein said system is metal coupler free.

4. A wood preservative system as defined in claim 3 wherein said $R^1$ is a $C_{10}$ alkyl group.

5. A wood preservative system comprising (A) a biocidal effective amount of at least one composition as defined in claim 1 and (B) a solvent.

6. A wood preservative system comprising (A) a biocidal effective amount of a composition as defined in claim 2 and (B) a solvent.

7. A wood preservative system as defined in claim 3 wherein said solvent is an aqueous solvent.

8. A wood preservative system as defined in claim 4 wherein said solvent is an aqueous solvent.

9. A wood preservative system as defined in claim 5 wherein said solvent is an aqueous solvent.

10. A wood preservative system as defined in claim 6 wherein said solvent is an aqueous solvent.

11. A wood preservative system as defined in claim 7 wherein said aqueous solvent is selected from the group consisting of water, aqueous ammonia, and aqueous ethanol.

12. A wood preservative system as defined in claim 8 wherein said aqueous solvent is selected from the group consisting of water, aqueous ammonia, and aqueous acetic acid.

13. A wood preservative system as defined in claim 9 wherein said aqueous solvent is selected from the group consisting of water, aqueous ammonia, and aqueous acetic acid.

14. A wood preservative system as defined in claim 10 wherein said aqueous solvent is selected from the group consisting of water, aqueous ammonia, and aqueous ethanol.

15. A wood preservative system as defined in claim 3 comprising from about 0.1 to about 5 parts by weight of di $C_8$–$C_{12}$ alkyl quaternary ammonium carbonate and from about 95 to about 99.9 parts by weight of solvent based upon 100 parts by weight of di $C_8$–$C_{12}$ alkyl quaternary ammonium carbonate and solvent combined.

16. A wood preservative system as defined in claim 15 comprising from about 1 to about 2 parts by weight of di $C_8$–$C_{12}$ alkyl quaternary ammonium carbonate and from about 98 to about 99 parts by weight of solvent based upon 100 parts by weight of di $C_8$–$C_{12}$ alkyl quaternary ammonium carbonate and solvent combined.

17. A wood preservative system as defined in claim 4 comprising from about 0.1 to about 5 parts by weight of didecyldimethylammonium carbonate and from about 95 to about 99.9 parts by weight of solvent based upon 100 parts by weight of didecyldimethylammonium carbonate and solvent combined.

18. A wood preservative system as defined in claim 17 comprising from about 1 to about 2 parts by weight of didecyldimethylammonium carbonate and from about 98 to about 99 parts by weight of solvent based upon 100 parts by weight of didecyldimethylammonium carbonate and solvent combined.

19. A wood preservative system as defined in claim 5 comprising from about 0.1 to about 5 parts by weight of (A) and from about 95 to about 99.9 parts by weight of (B) based upon 100 parts by weight of (A) and (B) combined.

20. A wood preservative system as defined in claim 19 comprising from about 1 to about 2 parts by weight of (A) and from about 98 to about 99 parts by weight of (B) based upon 100 parts by weight of (A) and (B) combined.

21. A wood preservative system as defined in claim 6 comprising from about 0.1 to about 5 parts by weight of (A) and from about 95 to about 99.9 parts by weight of (B) based upon 100 parts by weight of (A) and (B) combined.

22. A wood preservative system as defined in claim 21 comprising from about 1 to about 2 parts by weight of (A) and from about 98 to about 99 parts by weight of (B) based upon 100 parts by weight of (A) and (B) combined.

23. A method for preserving a wood substrate comprising treating said wood substrate with a wood preservative system as defined in claim 3.

24. A method for preserving a wood substrate comprising treating said wood substrate with a wood preservative system as defined in claim 4.

25. A method for preserving a wood substrate comprising treating said wood substrate with a wood preservative system as defined in claim 5.

26. A method for preserving a wood substrate comprising treating said wood substrate with a wood preservative system as defined in claim 6.

27. A $C_1$–$C_{20}$ alkyl or aryl-substituted alkyl, $C_8$–$C_{20}$ alkyl quaternary ammonium carbonate having the formula

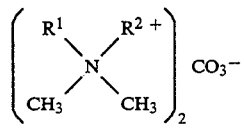

wherein $R^1$ is a $C_1$–$C_{20}$ alkyl or aryl-substituted alkyl group, and $R^2$ is a $C_8$–$C_{12}$ alkyl group, prepared by (a) reacting a $C_1$–$C_{20}$ alkyl or aryl-substituted alkyl, $C_8$–$C_{20}$ alkyl quaternary ammonium chloride reactant and a metal hydroxide reactant in a solvent comprising a $C_1$–$C_4$ normal alcohol, said metal hydroxide being present in an amount sufficient to yield a $C_1$–$C_{20}$ alkyl or aryl-substituted alkyl, $C_8$–$C_{20}$ alkyl quaternary ammonium hydroxide, a metal chloride, and optionally unreacted metal hydroxide; and (b) reacting said $C_1$–$C_{20}$ alkyl or aryl-substituted $C_8$–$C_{20}$ alkyl or aryl-substituted alkyl, $C_8$–$C_{20}$ alkyl quaternary ammonium hydroxide and optionally any unreacted metal hydroxide with carbon dioxide to yield said $C_1$–$C_{20}$ alkyl or aryl-substituted alkyl, $C_8$–$C_{20}$ alkyl quaternary ammonium carbonate and optionally a metal carbonate.

28. A di $C_8$–$C_{12}$ alkyl quaternary ammonium carbonate having the formula

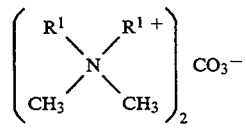

wherein $R^1$ is a $C_8$–$C_{12}$ alkyl group, prepared by (a) reacting a di $C_8$–$C_{12}$ alkyl quaternary ammonium chloride reactant and a metal hydroxide reactant in a solvent comprising a $C_1$–$C_4$ normal alcohol, said metal hydroxide being present in an amount sufficient to yield a di $C_8$–$C_{12}$ alkyl quaternary ammonium hydroxide, a metal chloride, and optionally unreacted metal hydroxide; and (b) reacting said di $C_8$–$C_{12}$ alkyl quaternary ammonium hydroxide and optionally unreacted metal hydroxide with carbon dioxide to yield said di $C_8$–$C_{12}$ alkyl quaternary ammonium carbonate and optionally a metal carbonate.

* * * * *